United States Patent
Chen et al.

(10) Patent No.: US 11,091,712 B1
(45) Date of Patent: Aug. 17, 2021

(54) METHOD FOR PRODUCING BIODIESEL AND TRIACETIN

(71) Applicant: Chin-Chang Chen, Taichung (TW)

(72) Inventors: Chin-Chang Chen, Taichung (TW); Jia-Hao Lin, Chiayi County (TW)

(73) Assignee: Chin-Chang Chen, Taichung (TW)

( * ) Notice: Subject to any disclaimer, the term of this patent is extended or adjusted under 35 U.S.C. 154(b) by 0 days.

(21) Appl. No.: 16/819,162

(22) Filed: Mar. 15, 2020

(51) Int. Cl.
  *C10L 1/02* (2006.01)
  *C11C 3/00* (2006.01)
  *C11C 3/10* (2006.01)
  *C07C 67/08* (2006.01)

(52) U.S. Cl.
  CPC .............. *C10L 1/026* (2013.01); *C07C 67/08* (2013.01); *C11C 3/003* (2013.01); *C11C 3/10* (2013.01); *C10L 2200/0476* (2013.01); *C10L 2200/0484* (2013.01); *C10L 2290/543* (2013.01)

(58) Field of Classification Search
  CPC .............. C10L 1/026; C10L 2290/543; C10L 2200/0484; C10L 2200/0476; C11C 3/003; C11C 3/10; C07C 67/08
  See application file for complete search history.

(56) References Cited

U.S. PATENT DOCUMENTS 8,754,253 B2 * 6/2014 Schuch .................. C07C 67/08
560/263

FOREIGN PATENT DOCUMENTS

| CN | 102994173 | * | 3/2013 |
| CN | 105087087 | * | 11/2015 |
| CN | 107032999 | * | 8/2017 |
| CN | 108034502 | * | 5/2018 |

* cited by examiner

*Primary Examiner* — Cephia D Toomer
(74) *Attorney, Agent, or Firm* — CKC & Partners Co., LLC

(57) ABSTRACT

A method for producing biodiesel and triacetin includes steps as follows. A bio-oil source is provided; the bio-oil source is palm oil acid or palm oil sludge. A bio-oil source pretreatment step is performed, wherein the bio-oil source is mixed with ash to decolor. A pre-esterification step is performed, wherein methanol and a pre-esterification catalyst are mixed, so as to form an organic phase solution and an aqueous phase solution. A transesterification step is performed, wherein the methanol and a lithium silicate catalyst are mixed, so as to form a crude biodiesel phase solution and a crude glycerol phase solution. A washing step is performed, wherein purified biodiesel is collected. A glycerol separating step is performed, wherein purified glycerol is collected. A glycerol esterification step is performed, wherein triacetin is collected.

9 Claims, 10 Drawing Sheets

METHOD FOR PRODUCING BIODIESEL AND TRIACETIN

BACKGROUND

Technical Field

The present disclosure relates to a method for producing biodiesel and triacetin. More particularly, the present disclosure relates to a method for producing biodiesel and triacetin using palm oil acid or palm oil sludge as a raw material.

Description of Related Art

Biodiesel is a clean alternative fuel, which is easy to use, biodegradable, non-toxic, and free of oil and aromatic chemicals. Biodiesel is a kind of biofuel that can replace petrochemical diesel by using animal and vegetable fats as a raw material. Biodiesel has the advantages of environmental friendliness, clean energy and decentralized energy supply, it is considered as one of an economical and potential energy alternatives.

Free fatty acid and vegetable or animal fats such as triglyceride can be transesterified to produce glycerin and biodiesel if alcohols and catalysts are added and mixed for a period of time. The transesterification reaction is a simple reversible reaction, if the raw materials are hydrolyzed, deteriorated or heated, the concentration of free fatty acids will increase usually. When a common sodium hydroxide basic catalyst is used for the transesterification reaction, the combination of sodium ions with free fatty acids produces saponification, making subsequent separation procedures more difficult.

Furthermore, the by-product of glycerol accompanying the transesterification reaction will be mass-produced after the biodiesel process becomes more and more important. Glycerol is a universally used by human and can be seen on general processes such as inexpensive chemical products, pharmaceutical, cosmetics, soap and toothpaste. If glycerol is only purified and sold, the excess glycerol will definitely impact the existing market.

Therefore, how to design a process for preparing biodiesel, and also make a reuse planning for glycerol, so as to achieve the economic benefits is the goal of the relevant industry.

SUMMARY

According to one aspect of the present disclosure, a method for producing biodiesel and triacetin includes steps as follows. A bio-oil source is provided, the bio-oil source is palm oil acid or palm oil sludge. A bio-oil source pretreatment step is performed, wherein the bio-oil source is mixed with ash to decolor, and moisture of the bio-oil source is removed. A pre-esterification step is performed, wherein methanol and a pre-esterification catalyst are mixed, then added to the bio-oil source dewatered to mix thoroughly, so as to form an organic phase solution and an aqueous phase solution, and the organic phase solution and the aqueous phase solution are separated by a centrifugation method. A transesterification step is performed, wherein the methanol and a lithium silicate catalyst are mixed, and then added to the organic phase solution to form a crude biodiesel phase solution and a crude glycerol phase solution, and the crude biodiesel phase solution and the crude glycerol phase solution are separated by a mechanical separation method. A washing step is performed, wherein the crude biodiesel phase solution is washed to remove the lithium silicate catalyst, and purified biodiesel is collected by the centrifugation method. A glycerol separating step is performed, wherein the crude glycerol phase solution is separated to remove the lithium silicate catalyst, so that purified glycerol is collected. A glycerol esterification step is performed, wherein the purified glycerol is reacted with acetic acid to form triacetin and reaction water, and the triacetin is collected.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1:
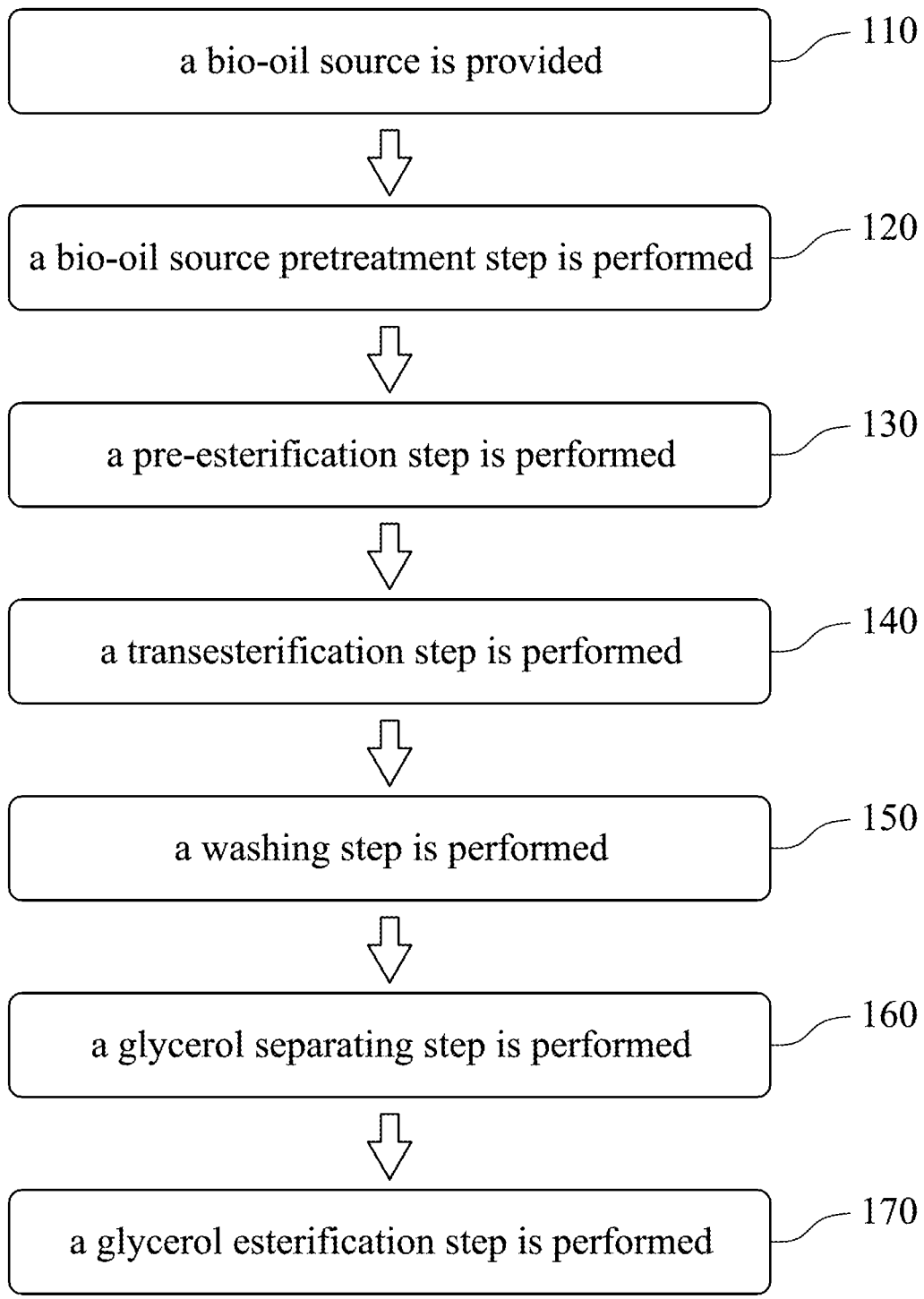
FIG. 1 is a flow chart of a method for producing biodiesel and triacetin according to one embodiment of the present disclosure.

The embodiments of the present disclosure will be described below by referring the figures. For the clarity, many practical details will be explained in the following description. However, the readers should realize that these practical details are not limited to the present disclosure. That is, in some embodiments of the present disclosure, the practical details are not necessary. In addition, in order to simplify the figures, some of the conventional structures and elements will be shown in the figures with simplified schematic; and the repeated elements will be shown by the same reference numerals.

Please refer to FIG. 1, which is a flow chart of a method for producing biodiesel and triacetin 100 according to one embodiment of the present disclosure. The method for producing biodiesel and triacetin 100 includes a step 110, a step 120, a step 130, a step 140, a step 150, a step 160 and a step 170.

In the step 110, a bio-oil source is provided, wherein the bio-oil source is palm oil acid or palm oil sludge. The palm oil is edible base oil. The oil acid and the oil sludge left over during the squeezing process are the accompanying scraps in the manufacturing process, which cannot be eaten by humans, but can be used as a source of free fatty acids.

In the step 120, a bio-oil source pretreatment step is performed, wherein the bio-oil source is mixed with ash to decolor, and moisture of the bio-oil source is removed.

In the step 130, a pre-esterification step is performed, wherein methanol and a pre-esterification catalyst are mixed, then added to the bio-oil source dewatered to mix thoroughly, so as to form an organic phase solution and an aqueous phase solution, and the organic phase solution and the aqueous phase solution are separated by a centrifugation method.

In the step 140, a transesterification step is performed, wherein the methanol and a lithium silicate catalyst are mixed, and then added to the organic phase solution to form a crude biodiesel phase solution and a crude glycerol phase solution, and the crude biodiesel phase solution and the crude glycerol phase solution are separated by a mechanical separation method.

In the step 150, a washing step is performed, wherein the crude biodiesel phase solution is washed to remove the lithium silicate catalyst, and purified biodiesel is collected by the centrifugation method.

In the step 160, a glycerol separating step is performed, wherein the crude glycerol phase solution is separated to remove the lithium silicate catalyst, so that purified glycerol is collected.

In the step 170, a glycerol esterification step is performed, wherein the purified glycerol is reacted with acetic acid to form triacetin and reaction water, and the triacetin is collected.

Figure 2:
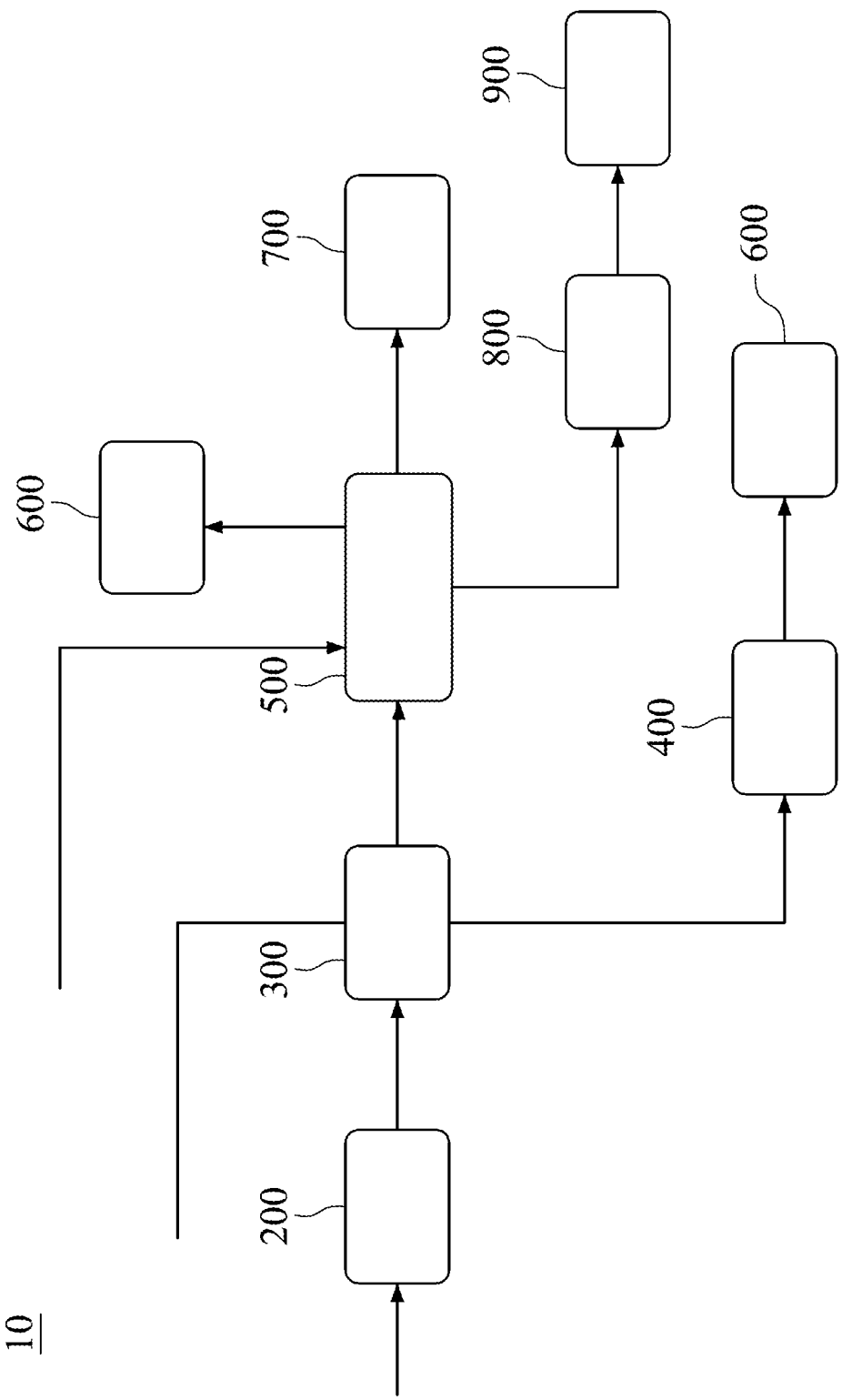
FIG. 2 is a schematic diagram of a biodiesel and triacetin producing system as shown in FIG. 1.

Please refer to FIG. 2, which is a schematic diagram of a biodiesel and triacetin producing system 10 as shown in FIG. 1. In FIG. 2, the biodiesel and triacetin producing system 10 includes a bio-oil source pretreatment system 200, a pre-esterification system 300, a pre-esterification catalyst recovery system 400, a transesterification system 500, two methanol recovery systems 600, a washing system 700, a glycerol separation system 800 and a glycerol esterification reaction system 900.

Specifically, the palm oil acid or the palm oil sludge is performed the pretreatment by the bio-oil source pretreatment system 200 first, and then transferred to the pre-esterification system 300 with the methanol and the sulfuric acid for the pre-esterification reaction. After the pre-esterification reaction, the aqueous phase solution is performed the catalyst recovery by the pre-esterification catalyst recovery system 400, and then performed the methanol recovery by the methanol recovery system 600. The organic phase solution is transferred to the transesterification system 500 with the methanol and the lithium silicate catalyst for the transesterification reaction. After the transesterification reaction, the crude biodiesel phase solution is transferred to the washing system 700 to collect the purified biodiesel. The crude glycerol phase solution is transferred to the glycerol separation system 800 to collect the purified glycerol, and the purified glycerol is transferred to the glycerol esterification reaction system 900 to perform the esterification reaction, so as to generate the triacetin. Furthermore, the excess methanol in the transesterification reaction is also performed the methanol recovery by the methanol recovery system 600, so as to enable to be reused.

The details of each steps of the method for producing biodiesel and triacetin 100 will be described in the following, and the related process systems are respectively matched.

In the step 110, the palm oil acid or the palm oil sludge is transferred to a storage tank by a tank truck, wherein the palm oil sludge may be solidified due to the low temperature. When the palm oil sludge is fed, the palm oil sludge is heated and melted by a dissolution tank, and then enters to the storage tank. The heating coil is disposed on the bottom of the storage tank to heat by the steam or the hot water and maintain the temperature of the palm oil acid or the palm oil sludge. The storage tank is equipped with a thermometer and a level gauge to monitor the operation amount and the temperature in the storage tank. In order to isolate the oil from deterioration caused by contacting air, the storage tank is designed with nitrogen seal.

Figure 3:
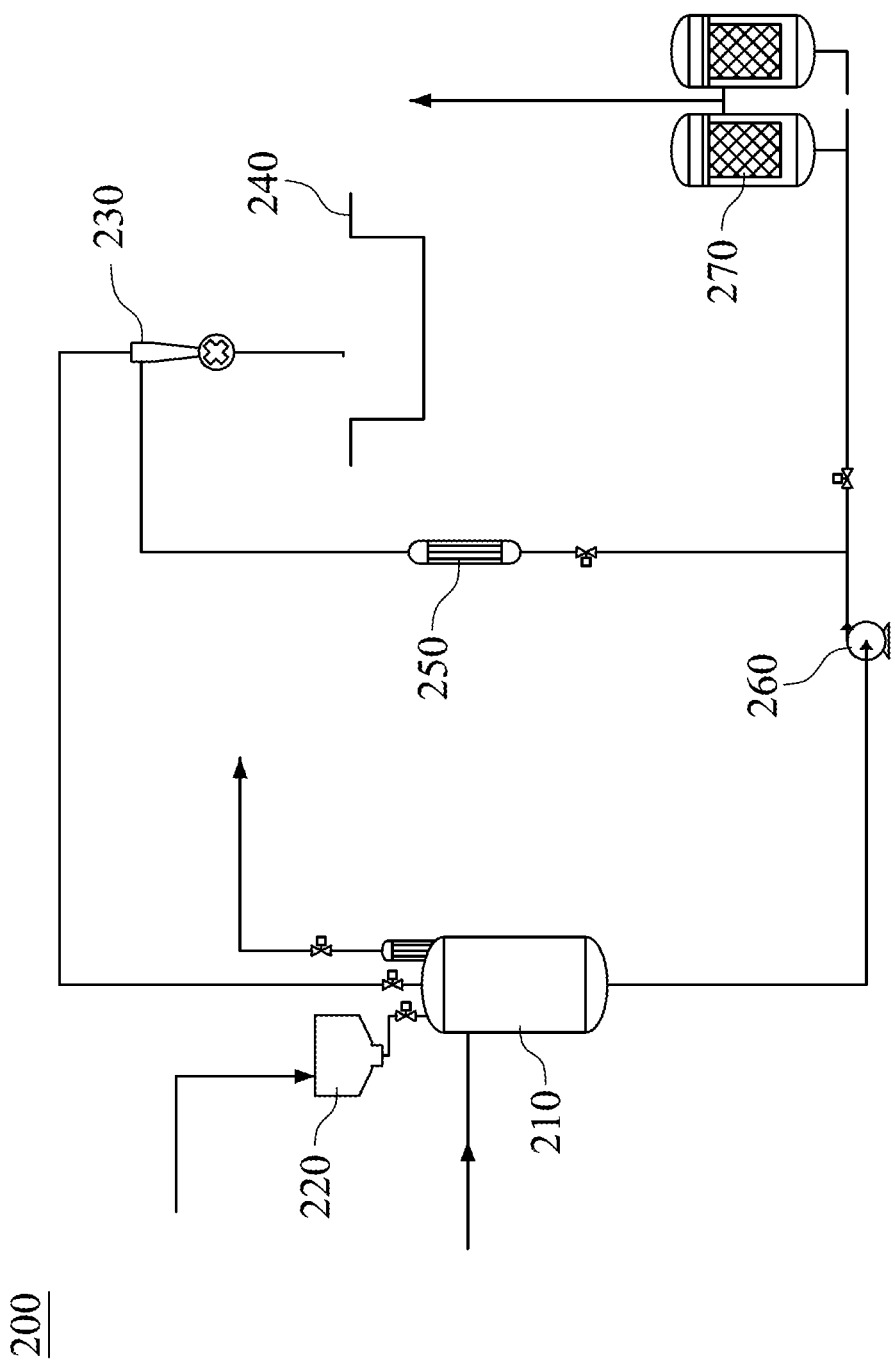
FIG. 3 is a schematic diagram of the bio-oil source pretreatment system as shown in FIG. 2.

In the step 120, the palm oil acid or the palm oil sludge is pressurized by a pump and sent from the tank area to the process area after metering. Please refer to FIG. 3, which is a schematic diagram of the bio-oil source pretreatment system 200 as shown in FIG. 2. In FIG. 3, the bio-oil source pretreatment system 200 includes a water removal tank 210, an ash feed tank 220, an ash separator 230, an ash tank 240, a recirculating heater 250, a palm oil pump 260 and a palm oil filtering tank 270.

Specifically, the palm oil acid or the palm oil sludge and the ash from the ash feed tank 220 enter the water removal tank 210 for mixing and decoloring. The heavy metals, the impurities, the moisture, and the colors that may remain in the palm oil acid or the palm oil sludge are absorbed by the high surface area of the ash. The ash can be but not limited to the banana ash or the straw ash, and during the process, the contact between the palm oil acid or the palm oil sludge and the ash is increased by cycling and stirring. After contacting 10 minutes to 30 minutes, the ash is transferred to the ash separator 230 to perform the solid-liquid separation. The separated ash is collected to the ash tank 240, and the liquid thrown from the ash is heated by the cyclic heating mechanism of the recirculating heater 250. Furthermore, the residual moisture in the palm oil acid or the palm oil sludge is volatilized by the difference of the boiling point. The water content of the palm oil acid or the palm oil sludge in the water removal tank 210 is reduced 300 ppm within 60 minutes. After the water content is reduced, the palm oil acid or the palm sludge is transferred to the palm oil filtering tank 270 via the palm oil pump 260. The multi-tube filter tank of the palm oil filtering tank 270 can block the ash that may remain, and the filter tank is provide with two groups, which can be operated by switching.

Figure 4:
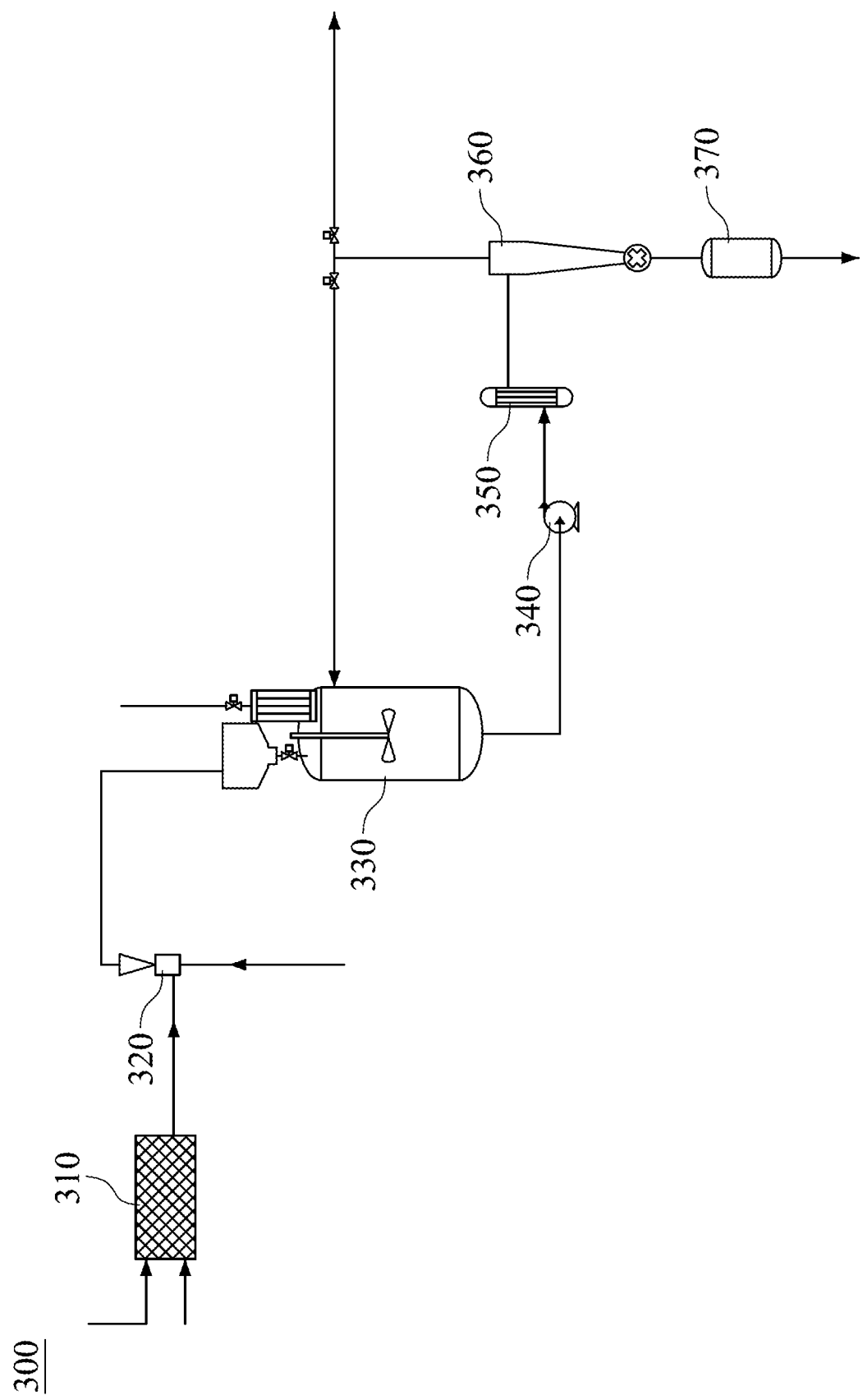
FIG. 4 is a schematic diagram of the pre-esterification system as shown in FIG. 2.

In the step 130, the methanol and the pre-esterification catalyst are pressurized by the pump and sent from the tank area to the process area after metering. The pre-esterification catalyst can be but not limited to sulfuric acid. Please refer to FIG. 4, which is a schematic diagram of the pre-esterification system 300 as shown in FIG. 2. In FIG. 4, the pre-esterification system 300 includes a mixing cooler 310, a pre-ester mixer 320, a pre-ester reactor 330, an oil-water pump 340, an oil-water cooler 350, a pre-ester separator 360 and a water phase tank 370.

Specifically, the methanol and the sulfuric acid enter the mixing cooler 310 for mixing. Since the sulfuric acid is mixed with the methanol, a large amount of heat of dilution is released, so that the large amount of heat of dilution can be removed by the cold water in the mixing cooler 310. After dewatering and filtering, the palm oil acid or the palm oil sludge and mixing solution of the methanol and the sulfuric acid are mixed by the mechanical structure of the pre-ester mixer 320 first, so that the methanol, the sulfuric acid and the palm oil acid or palm oil sludge are mixed thoroughly before entering the pre-ester reactor 330, reducing unnecessary mixing residence time in the pre-ester reactor 330 to reduce the size of the equipment.

The pre-esterification process is using the methanol and the palm oil acid or the palm oil sludge to perform the pre-esterification reaction under the sulfuric acid catalyst. The free fatty acid of the palm oil acid or the palm oil sludge is esterified first, and the overall reaction is in a homogeneous phase condition. The aforementioned pre-esterification reaction formula is represented by formula (I):

$$RCOOH + CH_3OH \rightarrow RCOO\text{---}CH_3 + H_2O \qquad \text{formula (I)}.$$

In the pre-ester reactor 330, the free fatty acid of the palm oil acid or the palm oil sludge is esterified with the methanol, and a temperature of the pre-esterification step can be range from 60° C. to 75° C. Under the condition of slightly lower than the boiling point of the methanol, the situation of losing a large amount of the methanol is not occurred, and the mixing effect in the pre-ester reactor 330 is increased because the methanol microbubbles which near the boiling point temperature during the operation. The retention time of the pre-esterification reaction is 2 hours to 3 hours, and the organic phase solution containing ester and the aqueous phase solution containing the methanol and the sulfuric acid are formed in the pre-ester reactor 330. The organic phase solution and the aqueous phase solution are transferred to the oil-water cooler 350 via the oil-water pump 340 for the temperature reduction, and then transferred to the pre-ester separator 360 after reducing the temperature. The organic phase solution and the aqueous phase solution are separated by the centrifugation method, and then the aqueous phase solution is transferred to the water phase tank 370 from the bottom of the per-ester separator 360 by metering for storage temporarily.

The step 130 can further include adding the methanol and the pre-esterification catalyst to the organic phase solution refluxed to perform a re-esterification reaction. Specifically, the organic phase solution separated from the per-ester separator 360 can be refluxed to the pre-ester reactor 330 and re-esterified with the methanol and the sulfuric acid, and then transferred to the pre-ester separator 360 for separating the organic phase solution and the aqueous phase solution by the centrifugation method to perform the subsequent processes.

Figure 5:
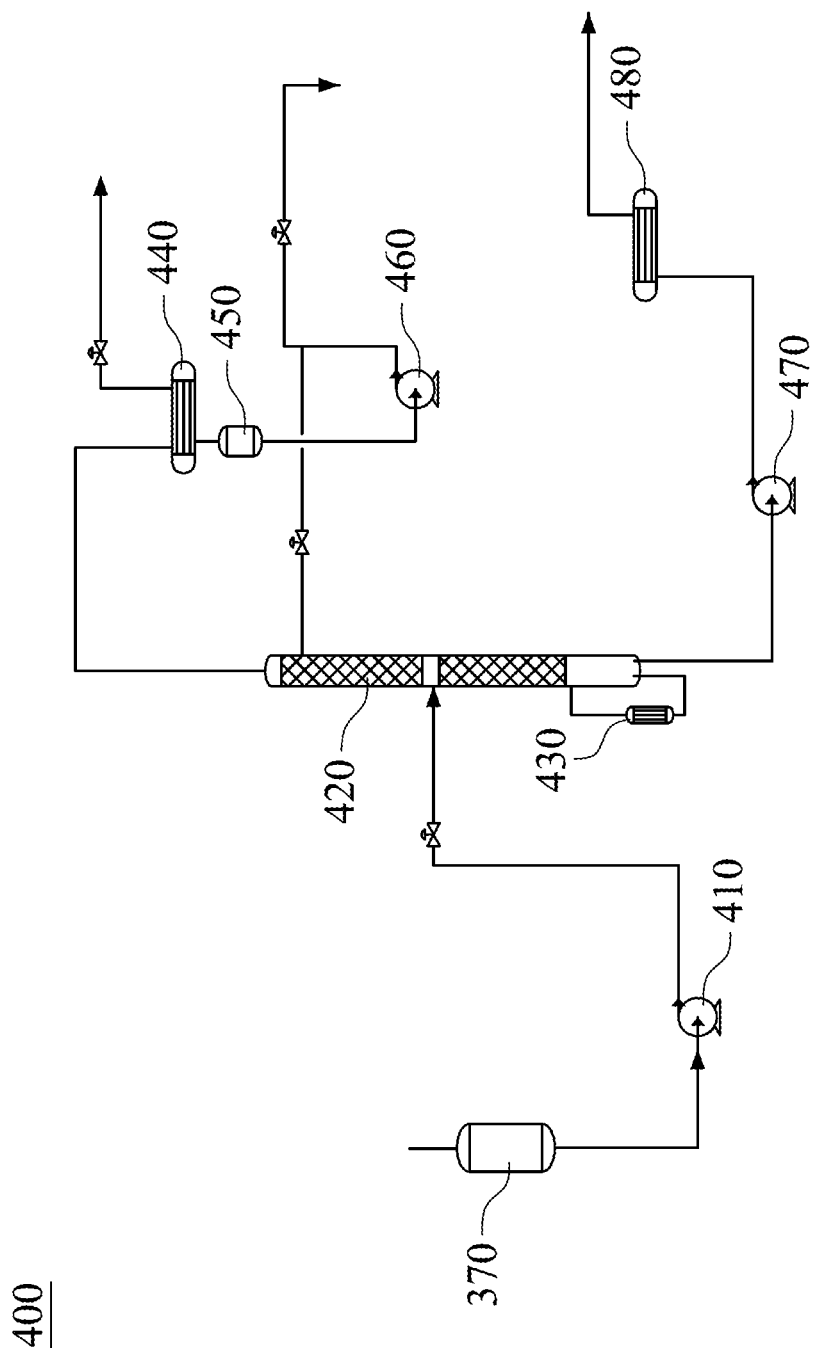
FIG. 5 is a schematic diagram of the pre-esterification catalyst recovery system as shown in FIG. 2.

Furthermore, the step 130 can further include recycling the pre-esterification catalyst of the aqueous phase solution by a vacuum distillation method. Please refer to FIG. 5, which is a schematic diagram of the pre-esterification catalyst recovery system 400 as shown in FIG. 2. In FIG. 5, the pre-esterification catalyst recovery system 400 includes a water phase pump 410, a catalyst distillation tower 420, a catalyst reboiler 430, a catalyst condenser 440, a catalyst reflux tank 450, a catalyst reflux pump 460, a catalyst tower bottom pump 470 and a catalyst tower bottom cooler 480.

Specifically, the aqueous phase solution is transferred to the catalyst distillation tower 420 from the water phase tank 370 via the water phase pump 410, and is fed in a stable flow control manner. The top of the catalyst distillation tower 420 uses cooling water for controlling the temperature and condensing, and the bottom of the catalyst distillation tower 420 uses heat transfer oil for controlling the temperature to operate. Under the vacuum condition, the low-boiling methanol and water are refluxed and collected at the top of the catalyst distillation tower 420 by the catalyst condenser 440, the catalyst reflux tank 450 and the catalyst reflux pump 460, and then sent to the subsequent methanol recovery tower (not shown) for performing the separation and the purification. The sulfuric acid is re-boiled and cycled by the catalyst reboiler 430, and then transferred to the catalyst tower bottom cooler 480 via the catalyst tower bottom pump 470. After cooling and collecting, the sulfuric acid is recycled to the sulfuric acid tank (not shown) in the system to recycle and reuse.

Figure 6:
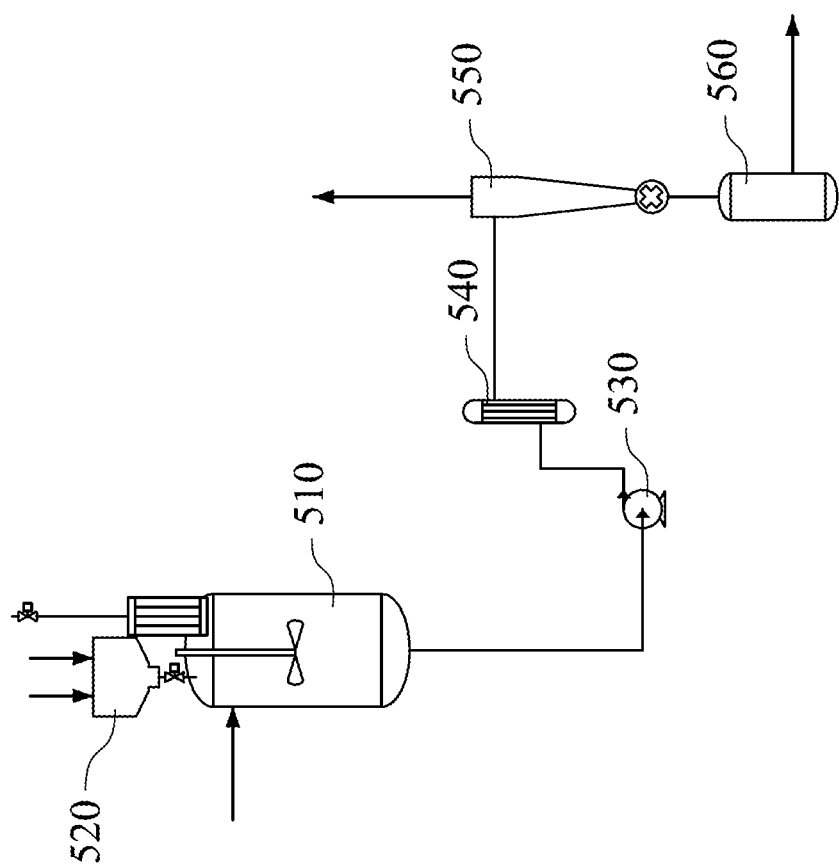
FIG. 6 is a schematic diagram of the transesterification system as shown in FIG. 2.

In the step 140, the organic phase solution separated from the pre-ester separator 360 is performed the subsequent transesterification reaction. Please refer to FIG. 6, which is a schematic diagram of the transesterification system 500 as shown in FIG. 2. In FIG. 6, the transesterification system 500 includes a trans-ester reactor 510, a trans-ester feed tank 520, a crude biodiesel pump 530, a crude biodiesel cooler 540, a trans-ester separator 550, and a crude glycerol tank 560.

Specifically, the organic phase solution is an intermediate after pre-esterifying. The organic phase solution contains the ester converted from the palm oil acid or the palm oil sludge and the free fatty acid, and sent to the trans-ester reactor 510 after pressurizing and metering. Furthermore, after mixing the methanol and the lithium silicate catalyst in the trans-ester feed tank 520, the mixing solution of the methanol and the lithium silicate catalyst is transferred to the trans-ester reactor 510 to perform the transesterification reaction with the organic phase solution. Triglyceride that in the palm oil acid or the palm oil sludge is used as a fatty acid source for biodiesel. The methanol, the palm oil acid or the palm oil sludge are performed in the trans-ester reactor 510 under a heterogeneous phase condition by the lithium silicate catalyst used in the present disclosure. The lithium silicate catalyst can be a lithium metasilicate catalyst or a lithium orthosilicate catalyst. The aforementioned transesterification reaction formula is represented by formula (II):

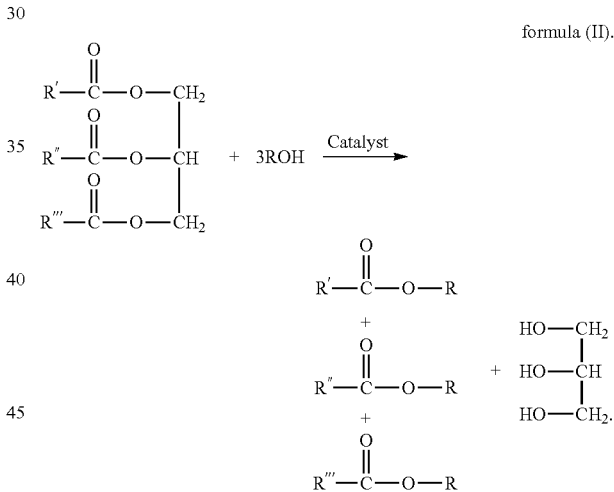

formula (II).

In the trans-ester reactor 510, the glyceride structure $OCH_2$ is truncated and the R group on the alcohol is converted, so as to form triplet fatty acid esters (biodiesel) and glycerol. The transesterification reaction is performed under the normal pressure, and a temperature of the transesterification step can be range from 60° C. to 75° C. The retention time of the transesterification reaction is 2 hours to 4 hours, and the crude biodiesel phase solution and the crude glycerol phase solution are formed in the trans-ester reactor 510. The crude biodiesel phase solution and the crude glycerol phase solution are immiscible with each other and have a density difference. The crude biodiesel phase solution and the crude glycerol phase solution are transferred to the crude biodiesel cooler 540 via the crude biodiesel pump 530 for the temperature reduction, and then transferred to the trans-ester separator 550 after reducing the temperature. The crude biodiesel phase solution and the crude glycerol phase solution are separated by the mechanical separation method.

Then, the crude glycerol phase solution is transferred to the crude glycerol tank 560 from the bottom of the trans-ester separator 550 by metering for storage temporarily, so as to continue the subsequent process.

Figure 7:
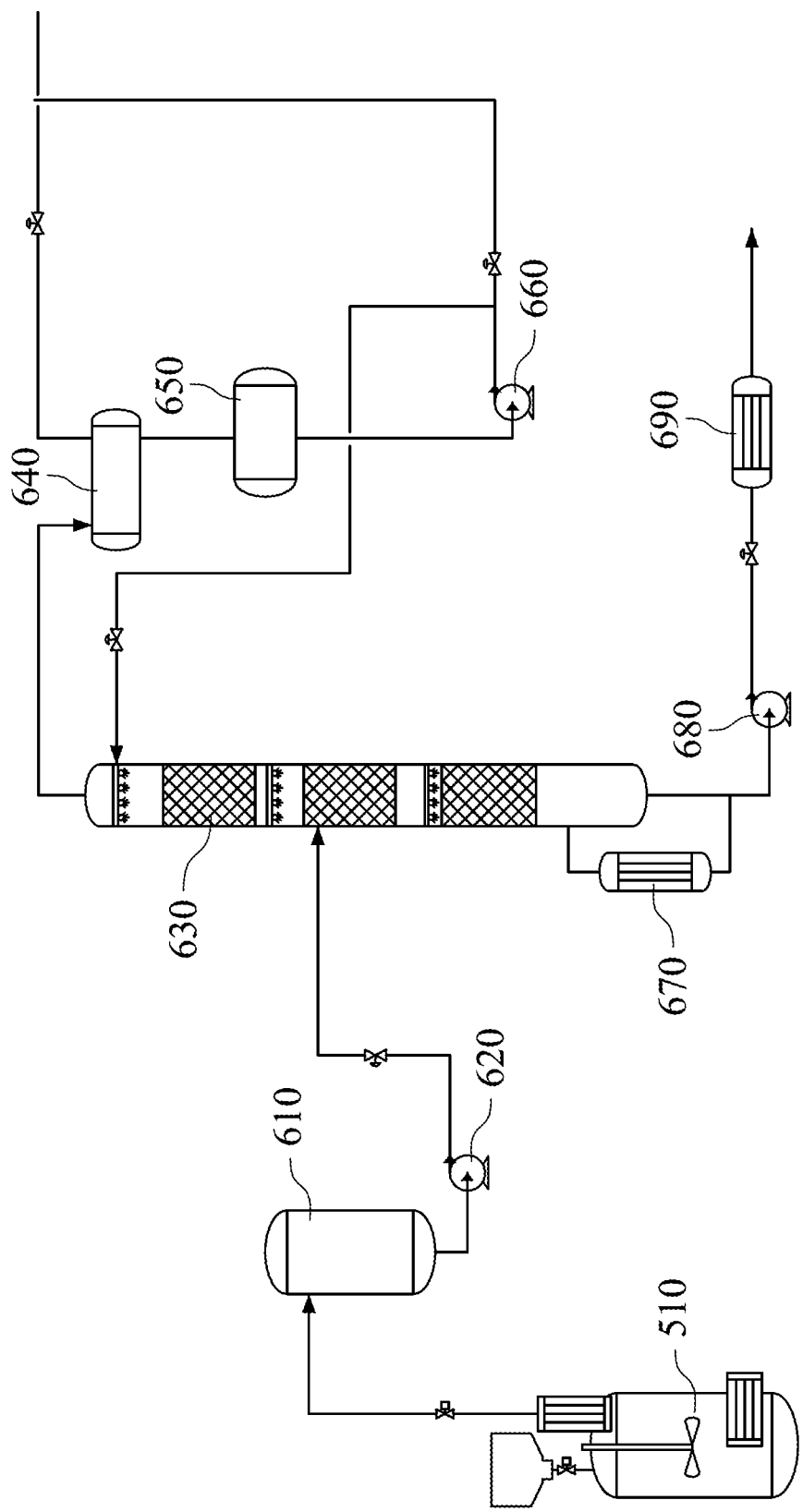
FIG. 7 is a schematic diagram of the methanol recovery system as shown in FIG. 2.

Furthermore, the step 140 can further include recycling the methanol by the vacuum distillation method. Please refer to FIG. 7, which is a schematic diagram of the methanol recovery system 600 as shown in FIG. 2. In FIG. 7, the methanol recovery system 600 includes a methanol tank 610, a methanol pump 620, a methanol recovery tower 630, a methanol condenser 640, a methanol reflux tank 650, a methanol reflux pump 660, a wastewater reboiler 670, a wastewater tower bottom pump 680 and a wastewater recovery cooler 690.

Specifically, due to the addition of excess methanol during the transesterification process, the methanol and water are transferred to the methanol recovery system 600 from the trans-ester reactor 510. The collected methanol and water are stored in the methanol tank 610 first, and then enter the methanol recovery tower 630 via the methanol pump 620 in a stable flow control manner. The methanol and water are separated and purified by the different boiling points. The methanol is collected at the top of the methanol recovery tower 630, and water is outflowed at the bottom of the methanol recovery tower 630. The whole methanol recovery system 600 can be operated at the normal pressure. The methanol obtained at the top of the methanol recovery tower 630 is refluxed and collected by the methanol condenser 640, the methanol reflux tank 650 and the methanol reflux pump 660, and then recycled to the process for continued use. Water obtained at the bottom of the methanol recovery tower 630 is re-boiled and cycled by the wastewater reboiler 670, and then transferred to the wastewater recovery cooler 690 via the wastewater tower bottom pump 680 for cooling, so as to transfer to the wastewater treatment. Moreover, the methanol in the step 130 can also be separated and purified by the methanol recovery system 600, and will not be described herein.

Figure 8:
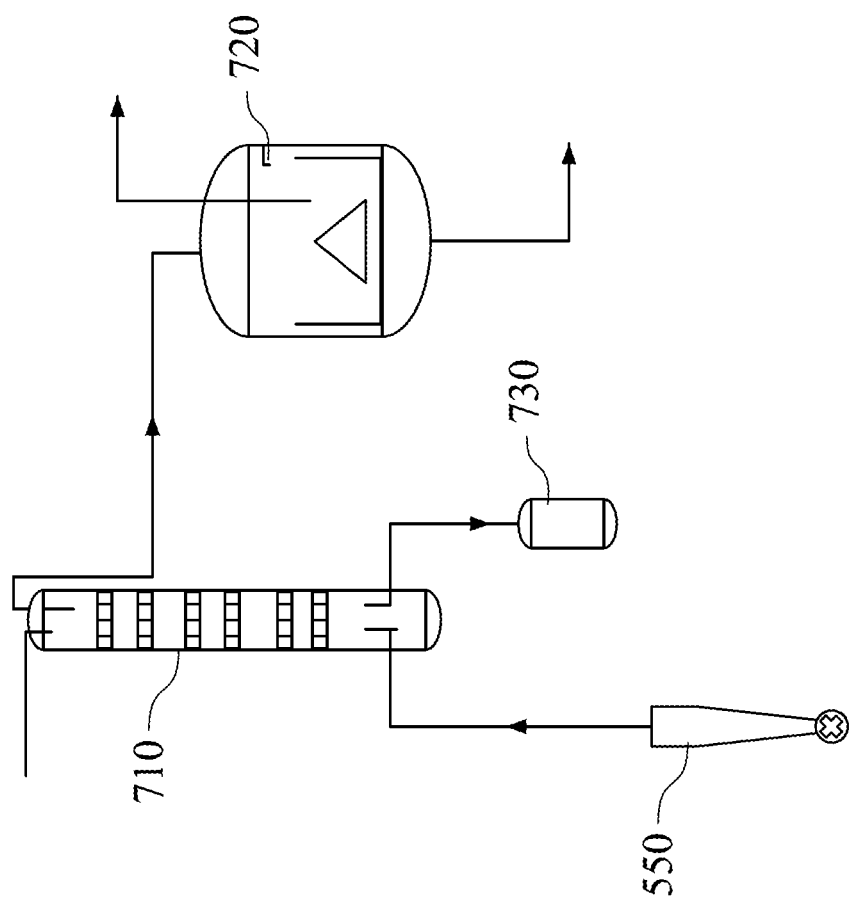
FIG. 8 is a schematic diagram of the washing system as shown in FIG. 2.

In the step 150, the separated crude biodiesel phase solution is transferred to the washing system 700 from the trans-ester separator 550. Please refer to FIG. 8, which is a schematic diagram of the washing system 700 as shown in FIG. 2. In FIG. 8, the washing system 700 includes a washing tower 710, a centrifuge 720, and a wastewater tank 730.

Specifically, the crude biodiesel phase solution is transferred to the washing tower 710 from the trans-ester separator 550, and performed the countercurrent contact with water. The lithium silicate catalyst that may be contained in the crude biodiesel phase solution is washed out by using water. The washing process is performed at the normal temperature and pressure, and then the waste water generated after washing is transferred to the wastewater tank 730. Furthermore, the washed crude biodiesel phase solution is transferred to the centrifuge 720, and the purified biodiesel is collected by the high-speed centrifugation. The vacuum condition is used during the centrifugation process, the remaining methanol in the biodiesel is separated, and the purified biodiesel is transferred to the tank area for storage.

Figure 9:
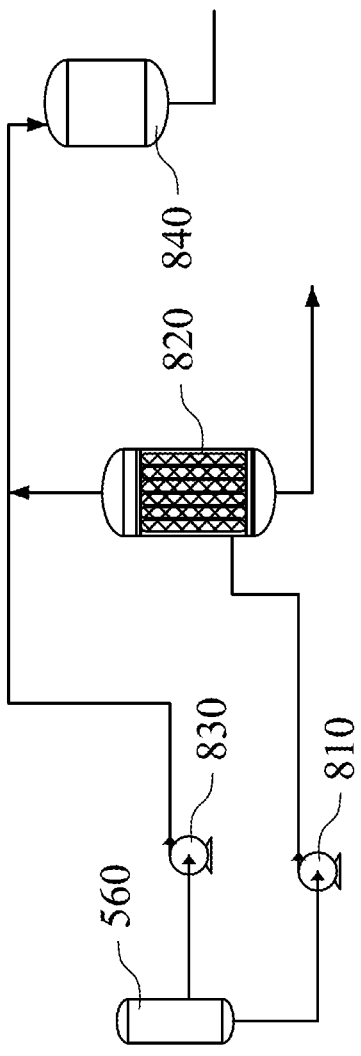
FIG. 9 is a schematic diagram of a glycerol separation system as shown in FIG. 2.

In the step 160, the catalyst miscellaneous liquid contained in the crude glycerol phase solution can be separated from the crude glycerol tank 560. Please refer to FIG. 9, which is a schematic diagram of a glycerol separation system 800 as shown in FIG. 2. In FIG. 9, the glycerol separation system 800 includes a catalyst miscellaneous liquid pump 810, a catalyst filter 820, a glycerol pump 830 and a glycerol tank 840.

Specifically, the catalyst miscellaneous liquid includes the lithium silicate catalyst and the high-density substance of the glycerol, and the catalyst miscellaneous liquid is transferred to the catalyst filter 820 via the catalyst miscellaneous liquid pump 810 to perform the solid-liquid separation. The collected lithium silicate catalyst can be continuously used in a recirculation system (not shown) by a suspension cycle method, and an appropriate amount of supplementation can be performed according to the catalyst activity and the reaction conversion rate. The purified glycerol after separating is transferred to the glycerol tank 840 via the glycerol pump 830, and the filtered high-density substance of the glycerol is also added in the purified glycerol, so as to perform the subsequent process.

Figure 10:
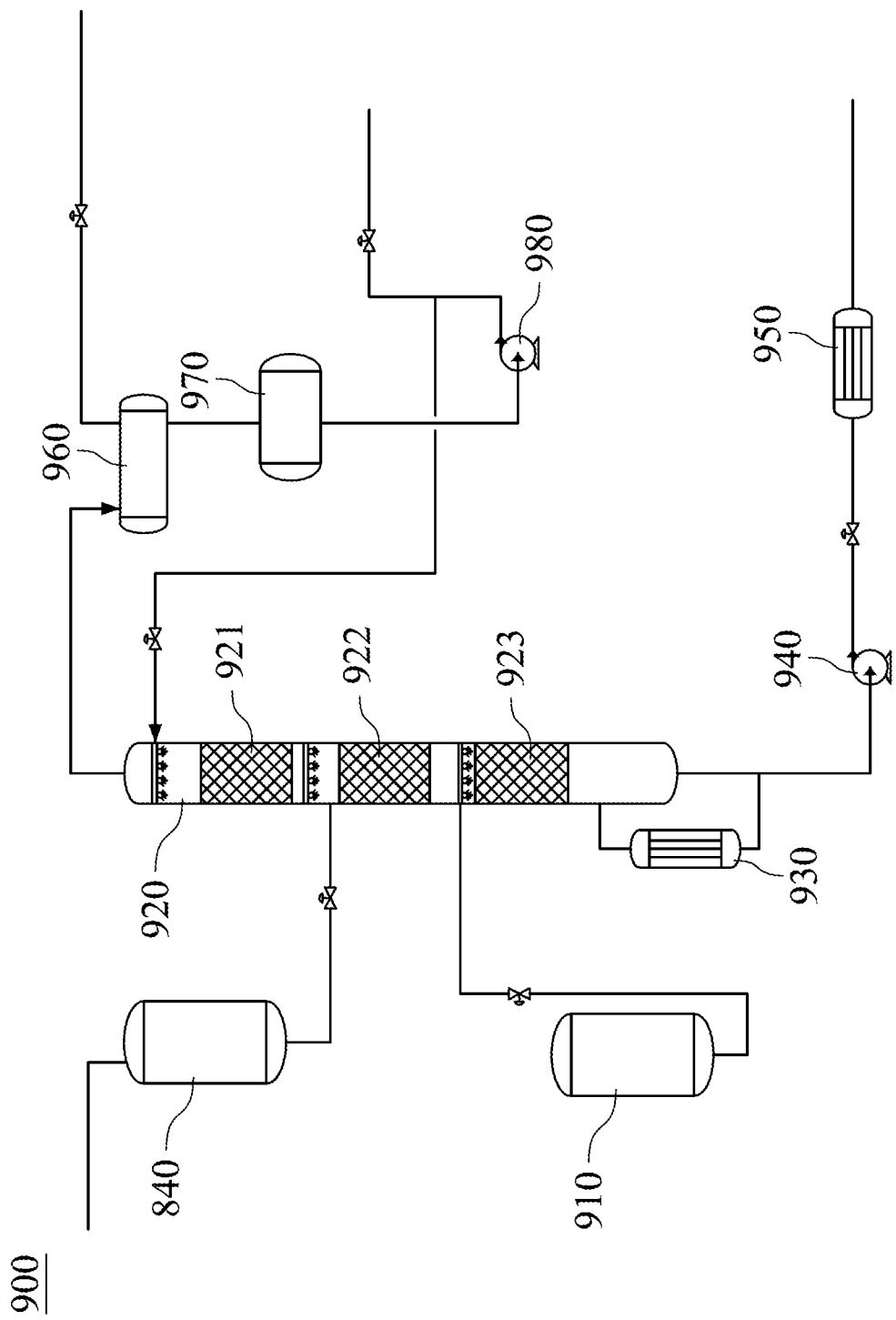
FIG. 10 is a schematic diagram of the glycerol esterification reaction system as shown in FIG. 2.

In the step 170, the purified glycerol is transferred to the glycerol esterification reaction system 900 from the glycerol tank 840. Please refer to FIG. 10, which is a schematic diagram of the glycerol esterification reaction system 900 as shown in FIG. 2. In FIG. 10, the glycerol esterification reaction system 900 includes an acetic acid tank 910, a reactive distillation tower 920, a triacetin reboiler 930, a triacetin tower bottom pump 940, a triacetin cooler 950, a reaction water condenser 960, a reaction water reflux tank 970 and a reaction water reflux pump 980.

Specifically, the purified glycerol and the acetic acid of the acetic acid tank 910 are transferred to the reactive distillation tower 920 in a stable flow control manner for performing the esterification reaction. The reactive distillation tower 920 is divided into a distillation section 921, a reaction section 922, and a stripping section 923. Using the difference of boiling points of the purified glycerol and the acetic acid, the purified glycerol enters to the distillation section 921, and the acetic acid enters to the stripping section 923. The purified glycerol with high-boiling point can be moved downward in the reactive distillation tower 920, and the acetic acid with the low-boiling point can be moved upward in the reactive distillation tower 920. Then, the purified glycerol and the acetic acid are contacted continuously in a reverse manner in the reaction section 922, so as to perform the esterification reaction. The glycerol esterification reaction system 900 is operated under the vacuum condition. Through the control of a tower temperature, an amount of reflow and a reaction output, the azeotropic phenomenon between ester, alcohol, and water in the esterification reaction can be eliminated, and the reaction conditions and quality control of the reactive distillation tower 920 can be stabilized. After the operation of the reactive distillation tower 920, the triacetin and the reaction water can be obtained. The triacetin at the bottom of the reactive distillation tower 920 is re-boiled and cycled by the triacetin reboiler 930, and then transferred to the triacetin cooler 950 via the triacetin tower bottom pump 940 for cooling, so as to transfer to the tank area for storage. The reaction water at the top of reactive distillation tower 920 is refluxed and collected by the reaction water condenser 960, the reaction water reflux tank 970 and the reaction water reflux pump 980, and then transferred to the wastewater treatment.

Therefore, the method for producing biodiesel and triacetin 100 uses the palm oil acid or the palm oil sludge as a source of fatty acid, and performs the pre-esterification reaction and the transesterification reaction with the methanol and the catalyst to produce the biodiesel. The glycerol intermediate produced in the transesterification reaction uses the reuse method to perform the esterification reaction with the acetic acid to form a higher-priced triacetin. The whole process includes the raw material pretreatment, pre-esterification, transesterification, catalyst recovery, methanol recovery, biodiesel separation and purification, and esterification reaction process of glycerol reuse.

Example

1. Specifications of Palm Oil Sludge

The palm oil sludge is used as the raw material of the present disclosure, and the specifications of the palm oil sludge are shown in Table 1.

TABLE 1

| Specifications | palm oil sludge |
|---|---|
| moisture | 11420 mg/kg |
| viscosity (40° C.) | 29.2 mm$^2$/s |
| density (15° C.) | 911.7 kg/m$^3$ |
| acid value | 175.5 mgKOH/g |
| iodine value | 87.42 gI$_2$/100 g |

2. Preparation of Lithium Silicate Catalyst

The rice husk ash or the burned ash is mixed with lithium oxide and lithium carbonate and ground into the uniform powder, and then calcined in the air environment at 900° C. for 4 hours to obtain the lithium metasilicate catalyst and the lithium orthosilicate catalyst, respectively.

3. Pre-Esterification Process

First, sulfuric acid and methanol are mixed with the palm oil sludge at the pre-ester mixer. Then, the palm oil sludge, the methanol and the sulfuric acid are transferred to the pre-ester reactor, and placed on the heating stirrer. A condensing and refluxing device is mounted on the pre-ester reactor, and the pre-esterification reaction is performed at 300-900 rpm and 60-75° C. for 1-4 hours. After 4 hours of reaction, the pre-esterified solution is transferred to the pre-ester separator to stand for cool down and separate layers. The upper organic phase solution is taken to continue the transesterification reaction.

Furthermore, the organic phase solution is refluxed to the pre-ester reactor, the same amount of the methanol and the sulfuric acid are added in the pre-ester reactor, and then react again for 4 hours to perform the re-esterification. Next, the re-esterified solution is transferred to the pre-ester separator to stand for cool down and separate layers. The upper organic phase solution is taken to continue the transesterification reaction.

4. Transesterification Process

First, the lithium silicate catalyst and methanol are mixed with the organic phase solution at the trans-ester reactor, and placed on the heating stirrer. A condensing and refluxing device is mounted on the trans-ester reactor, and the transesterification reaction is performed at 300-900 rpm and 60-75° C. for 1-3 hours. After 3 hours of reaction, the trans-esterified solution is transferred to the trans-ester separator to stand for cool down and separate layers. The upper crude biodiesel phase solution is taken, washed with 0° C. deionized water, and then centrifuged at 4000 rpm for 60 minutes to obtain the purified biodiesel. The methanol is removed by suction.

5. Results of Transesterification Ratio 5.1 Pre-Ester Oil-Alcohol Ratio

The results of transesterification ratio of different pre-ester oil-alcohol ratio with fixed sulfuric acid content, lithium silicate catalyst content and trans-ester oil-alcohol ratio are shown in Table 2.

TABLE 2

|  | Example 1 | Example 2 | Example 3 |
|---|---|---|---|
| sulfuric acid content | 9 wt % | 9 wt % | 9 wt % |
| pre-ester oil-alcohol ratio | 1:9 | 1:12 | 1:18 |
| lithium silicate catalyst content | 6 wt % | 6 wt % | 6 wt % |
| trans-ester oil-alcohol ratio | 1:18 | 1:18 | 1:18 |
| transesterification ratio | 80.13% | 71.44% | 70.16% |

|  | Example 4 | Example 5 |
|---|---|---|
| sulfuric acid content | 9 wt % | 6 wt % |
| pre-ester oil-alcohol ratio | 1:24 | 1:0.12 (w/w) |
| lithium silicate catalyst content | 6 wt % | 6 wt % |
| trans-ester oil-alcohol ratio | 1:18 | 1:18 |
| transesterification ratio | 71.67% | 69.74% |

|  | Example 6 | Example 7 |
|---|---|---|
| sulfuric acid content | 6 wt % | 6 wt % |
| pre-ester oil-alcohol ratio | 1:0.24 (w/w) | 1:0.3 (w/w) |
| lithium silicate catalyst content | 6 wt % | 6 wt % |
| trans-ester oil-alcohol ratio | 1:18 | 1:18 |
| transesterification ratio | 70.18% | 69.90% |

5.2 Lithium Silicate Catalyst Content Ratio

The results of transesterification ratio of different lithium silicate catalyst content with fixed sulfuric acid content, pre-ester oil-alcohol ratio and trans-ester oil-alcohol ratio are shown in Table 3.

TABLE 3

|  | Example 8 | Example 9 |
|---|---|---|
| sulfuric acid content | 9 wt % | 9 wt % |
| pre-ester oil-alcohol ratio | 1:0.3 (w/w) | 1:0.3 (w/w) |
| lithium silicate catalyst content | 6 wt % | 8 wt % |
| trans-ester oil-alcohol ratio | 1:24 | 1:24 |
| transesterification ratio | 80.13% | 85.87% |

5.3 Trans-Ester Oil-Alcohol Ratio

The results of transesterification ratio of different trans-ester oil-alcohol ratio with fixed sulfuric acid content, pre-ester oil-alcohol ratio and lithium silicate catalyst content are shown in Table 4.

TABLE 4

|  | Example 10 | Example 11 | Example 12 |
|---|---|---|---|
| sulfuric acid content | 9 wt % | 9 wt % | 9 wt % |
| pre-ester oil-alcohol ratio | 1:0.3 (w/w) | 1:0.3 (w/w) | 1:0.3 (w/w) |
| lithium silicate catalyst content | 6 wt % | 6 wt % | 6 wt % |
| trans-ester oil-alcohol ratio | 1:6 | 1:9 | 1:12 |
| transesterification ratio | 72.18% | 77.49% | 85.28% |

TABLE 4-continued

| | Example 13 | Example 14 |
|---|---|---|
| sulfuric acid content | 9 wt % | 9 wt % |
| pre-ester oil-alcohol ratio | 1:0.3 (w/w) | 1:0.3 (w/w) |
| lithium silicate catalyst content | 6 wt % | 6 wt % |
| trans-ester oil-alcohol ratio | 1:18 | 1:24 |
| transesterification ratio | 73.86% | 80.13% |

6. Specifications of Biodiesel

Please refer to Table 5, which is a specification of the biodiesel produced from the palm oil sludge, and the biodiesel is complied with the standard of CNS-15072.

TABLE 5

| specification | biodiesel | CNS-15072 |
|---|---|---|
| Ester content | 96.95 | >96.5 |
| Moisture | 191 | <500 |
| Viscosity (40° C.) | 4.70 | 3.5~5.0 |
| Density (15° C.) | 887 | 860-900 |
| Sulfur content | 8.5 | <10 |
| Phosphorus content | 1.2 | <4 |
| Acid value | 0.3 | <0.5 |
| Iodine value | 92 | <120 |
| Monoglyceride content | 0.09 | <0.8 |
| Diglyceride content | 0.01 | <0.2 |
| Triglyceride content | 0.01 | <0.2 |
| Alkali Metals (Na + K) | 2.1 | <5 |
| Alkali Metals (Ca + Mg) | 2.5 | <5 |
| Free Glycerine | 0.0017 | <0.02 |
| Total Glycerine | 0.04 | <0.25 |
| Cold filter plugging point | −1 | <0 |
| Flash point | 138 | >120 |
| Tar remnant (at 10% distillation remnant) | 0.02 | <0.3 |
| Cetane Number | 63 | >51 |
| Sulphated ash content | 0.001 | <0.02 |
| Total contamination | 20 | <24 |
| Copper band corrosion (3 hours at 50° C.) | Class 1 | Class 1 |

In conclusion, the method for producing biodiesel and triacetin of the present disclosure is using the palm oil acid or the palm oil sludge to produce the biodiesel, and the reuse of glycerol is planned. The formed triacetin by the glycerol and the acetic acid is the second high-priced by-product in the method. If the method is scaled up to the test plant level, under the dual consideration of regional and the palm oil plant production, the biodiesel can be used in combination with the reuse of triacetin as the by-product of glycerol to establish the optimal conditions, so as to achieve the highest efficiency, the most stable quality, the lowest energy consumption and the lowest production costs.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A method for producing biodiesel and triacetin, comprising:
    providing a bio-oil source, the bio-oil source is palm oil acid or palm oil sludge;
    performing a bio-oil source pretreatment step, wherein the bio-oil source is mixed with ash to decolor, and moisture of the bio-oil source is removed to form a dewatered bio-oil source;
    performing a pre-esterification step, wherein methanol and a pre-esterification catalyst are mixed, the mixture is added to said dewatered bio-oil source, mixed and heated, so as to form an organic phase solution and an aqueous phase solution, and the organic phase solution and the aqueous phase solution are separated by a centrifugation method;
    performing a transesterification step, wherein methanol and a lithium silicate catalyst are mixed, added to the organic phase solution and heated, so as to form a crude biodiesel phase solution and a crude glycerol phase solution, and the crude biodiesel phase solution and the crude glycerol phase solution are separated by a mechanical separation method;
    performing a washing step, wherein the crude biodiesel phase solution is washed to remove the lithium silicate catalyst, and purified biodiesel is collected by the centrifugation method;
    performing a glycerol separating step, wherein the crude glycerol phase solution is separated to remove the lithium silicate catalyst, so that purified glycerol is collected; and
    performing a glycerol esterification step, wherein the purified glycerol is reacted with acetic acid to form triacetin and reaction water, and the triacetin is collected.

2. The method for producing biodiesel and triacetin of claim 1, wherein the pre-esterification catalyst is sulfuric acid.

3. The method for producing biodiesel and triacetin of claim 1, wherein a temperature of the pre-esterification step ranges from 60° C. to 75° C.

4. The method for producing biodiesel and triacetin of claim 1, wherein the pre-esterification step further comprises:
    recycling the pre-esterification catalyst of the aqueous phase solution by a vacuum distillation method.

5. The method for producing biodiesel and triacetin of claim 1, wherein the lithium silicate catalyst is a lithium metasilicate catalyst or a lithium orthosilicate catalyst.

6. The method for producing biodiesel and triacetin of claim 1, wherein a temperature of the transesterification step ranges from 60° C. to 75° C.

7. The method for producing biodiesel and triacetin of claim 1, wherein the transesterification step further comprises:
    recycling the methanol by a vacuum distillation method.

8. The method for producing biodiesel and triacetin of claim 1, wherein the glycerol separating step further comprises:
    collecting the lithium silicate catalyst by a filtering method, and the lithium silicate catalyst is refluxed.

9. The method for producing biodiesel and triacetin of claim 1, wherein in the glycerol esterification step, the triacetin and the reaction water are separated by a vacuum distillation method.

* * * * *